US008449518B2

United States Patent
Allison-Rogers (10) Patent No.: US 8,449,518 B2
(45) Date of Patent: May 28, 2013

(54) DISPOSABLE NAPPY WITH SEPARATE BELT OR LEG GUARDS FORMED FROM LAMINATE OUTER COVER

(75) Inventor: Susan M. Allison-Rogers, Tasmania (AU)

(73) Assignee: Kuver Designs Pty Ltd, Tasmania (AU)

( * ) Notice: Subject to any disclaimer, the term of this patent is extended or adjusted under 35 U.S.C. 154(b) by 573 days.

(21) Appl. No.: 12/450,409

(22) PCT Filed: Oct. 2, 2008

(86) PCT No.: PCT/AU2008/001462
§ 371 (c)(1),
(2), (4) Date: Sep. 23, 2009

(87) PCT Pub. No.: WO2009/043101
PCT Pub. Date: Apr. 9, 2009

(65) Prior Publication Data
US 2010/0036340 A1 Feb. 11, 2010

(30) Foreign Application Priority Data
Oct. 2, 2007 (AU) ............................... 2007905385

(51) Int. Cl.
*A61F 13/64* (2006.01)
*A61F 13/56* (2006.01)

(52) U.S. Cl.
USPC ............................. 604/392; 604/386; 604/374

(58) Field of Classification Search
USPC ............................. 604/367, 385.28, 392, 391
See application file for complete search history.

(56) References Cited

U.S. PATENT DOCUMENTS

| | | | |
|---|---|---|---|
| 780,598 A | 1/1905 | Coleman et al. |
| 1,507,180 A | 9/1924 | Wells |
| 1,695,153 A | 12/1928 | Nelson |
| 2,571,357 A | 10/1951 | Gemora |
| 2,840,078 A | 6/1958 | Smith |
| 3,117,577 A | 1/1964 | Mosier |
| 3,225,765 A | 12/1965 | Mosier et al. |
| 3,653,381 A | 4/1972 | Warnken |
| 4,019,517 A | 4/1977 | Glassman |
| 4,265,245 A | 5/1981 | Glassman |
| 4,759,754 A | 7/1988 | Korpman |
| 4,964,860 A | 10/1990 | Gipson et al. |
| 5,019,064 A | 5/1991 | Eilender |

(Continued)

FOREIGN PATENT DOCUMENTS

| AU | 714528 | 1/2000 |
|---|---|---|
| CA | 2255465 | 4/2000 |

(Continued)

OTHER PUBLICATIONS

International Search Report for PCT/AU2008/001462 (Dec. 8, 2008).

*Primary Examiner* — Susan Su
(74) *Attorney, Agent, or Firm* — Klarquist Sparkman, LLP (57) ABSTRACT

A disposable nappy includes a disposable nappy body portion (3) and a separate belt (5) to secure the nappy body to the person. The belt includes a number of Velcro-type fastener portions that attach to a cover stock material of the nappy. The cover stock material is of a material that includes fibers that can retain the Velcro-type fasteners. Also defined are leg guards (19) formed from outer edges of a laminate cover layer.

17 Claims, 4 Drawing Sheets

U.S. PATENT DOCUMENTS

| | | | |
|---|---|---|---|
| 5,135,522 A | 8/1992 | Fahrenkrug et al. | |
| 5,137,526 A | 8/1992 | Coates | |
| 5,190,533 A * | 3/1993 | Blackburn | 604/367 |
| 5,286,770 A | 2/1994 | Bastioli et al. | |
| 5,377,837 A * | 1/1995 | Roussel | 206/494 |
| 5,409,476 A | 4/1995 | Coates | |
| 5,422,387 A | 6/1995 | Toms et al. | |
| 5,669,901 A | 9/1997 | LaFortune et al. | |
| 5,722,127 A | 3/1998 | Coates | |
| 5,725,518 A | 3/1998 | Coates | |
| 5,752,946 A | 5/1998 | Boberg et al. | |
| 5,759,569 A | 6/1998 | Hird et al. | |
| 5,820,620 A | 10/1998 | Allison-Rogers | |
| 5,858,012 A | 1/1999 | Tamaki et al. | |
| 5,891,122 A | 4/1999 | Coates | |
| 6,231,970 B1 | 5/2001 | Andersen et al. | |
| 6,254,583 B1 | 7/2001 | Coates | |
| 6,312,420 B1 | 11/2001 | Sasaki et al. | |
| 6,334,858 B1 | 1/2002 | Ronnberg et al. | |
| 6,419,666 B1 | 7/2002 | Mishima | |
| 6,443,930 B1 | 9/2002 | Silverstein | |
| 6,569,141 B1 | 5/2003 | Bruemmer-Prestley et al. | |
| 6,623,466 B1 | 9/2003 | Richardson | |
| 6,648,868 B2 | 11/2003 | Sayama et al. | |
| 6,895,603 B2 | 5/2005 | Coates | |
| 6,926,705 B1 | 8/2005 | Coates | |
| 7,014,632 B2 | 3/2006 | Takino et al. | |
| 7,264,615 B2 | 9/2007 | Sherrod et al. | |
| 7,431,716 B2 | 10/2008 | Tracy | |
| 8,002,762 B2 | 8/2011 | Allison-Rogers | |
| 2002/0028857 A1 | 3/2002 | Holy | |
| 2002/0058920 A1 | 5/2002 | Toyoda et al. | |
| 2003/0120253 A1* | 6/2003 | Wentzel et al. | 604/392 |
| 2003/0145352 A1 | 7/2003 | Frohberg | |
| 2004/0158225 A1 | 8/2004 | Coates | |
| 2004/0210206 A1 | 10/2004 | Coates | |
| 2004/0236298 A1 | 11/2004 | Coates | |
| 2005/0210560 A1 | 9/2005 | Coates | |
| 2006/0167433 A1* | 7/2006 | D'Alcini | 604/392 |
| 2009/0054548 A1 | 2/2009 | Wang et al. | |
| 2009/0324917 A1 | 12/2009 | Wang et al. | |
| 2010/0016822 A1* | 1/2010 | Wickremesinghe | 604/375 |

FOREIGN PATENT DOCUMENTS

| | | |
|---|---|---|
| EP | 1142547 A1 | 10/2001 |
| FR | 2699813 A1 | 7/1994 |
| JP | 2002-325796 | 11/2002 |
| JP | 2003-175066 | 6/2003 |
| KR | 100457393 | 11/2004 |
| WO | WO 88/07335 | 10/1988 |
| WO | WO 93/23000 | 11/1993 |
| WO | WO 94/03137 | 2/1994 |
| WO | WO 96/34588 | 11/1996 |
| WO | WO 01/43682 | 6/2001 |
| WO | WO 02/067833 | 9/2002 |
| WO | WO 2008/095310 | 8/2008 |

\* cited by examiner

DISPOSABLE NAPPY WITH SEPARATE BELT OR LEG GUARDS FORMED FROM LAMINATE OUTER COVER

CROSS REFERENCE TO RELATED APPLICATIONS

This is the U.S. National Stage of International Application No. PCT/AU2008/001462, filed Oct. 2, 2008, which claims the benefit of Australian Patent Application No. 2007905385, filed Oct. 2, 2007.

The present invention relates to disposable nappies.

The present invention relates particularly, although by no means exclusively, to disposable nappies that are compostable.

The word "disposable" is understood herein to mean that the nappies are of a type that are intended for a single use only, as opposed to cloth nappies that are generally intended for multiple uses.

The word "nappy" is understood herein to be synonymous with the word "diaper".

The word "compostable" is understood herein to mean that the nappy body will disintegrate through biodegradation such that at least 90% of the material will pass through a 2 mm sieve after a 12 week test period under compost conditions as per Australian Standard AS4736-2006 or the equivalent International Standard.

The present invention also relates to a method of manufacturing nappies. The nappies may be disposable nappies that are compostable. However, the method is not confined to such nappies.

The development of disposable nappies that are compostable in accordance with the above definition is an important objective of the nappy industry. The environmental problems associated with non-compostable nappies are well documented. There are significant environmental advantages to be gained by the introduction of compostable nappies in accordance with the above definition into the market. It has been a long-standing objective of the nappy industry to produce such truly compostable nappies. There have been a number of claims made that new nappy products are compostable. However, as far as the applicant can determine, the claims are not correct and the applicant is not aware of any nappies that can fairly be said to be compostable in accordance with the above definition.

The present invention is not confined to disposable nappies that can be produced as compostable nappies in accordance with the above definition and is equally applicable to disposable nappies that are not compostable in accordance with the above definition.

In broad terms the disposable nappy of the present invention comprises (a) a disposable nappy body, preferably made with compostable materials in accordance with the above definition to enable easy, economical "recycling" of a used nappy through domestic or commercial composting, and (b) a reusable (may be recyclable and/or compostable) removable fastening belt to minimise resources used in each nappy and to provide a better fit than traditional side tape fasteners with elastic waist fittings.

According to the present invention there is provided a disposable nappy that comprises:

(a) a disposable nappy body that is shaped to fit around a crotch region of a person wearing the nappy; and (b) a separate belt to secure the nappy body to the person, wherein the belt includes one or more than one Velcro-type fastener and the body of the nappy includes an outer coverstock of a material at least in the region that is contacted by the belt that has fibres that can retain the Velcro-type fastener or fasteners.

In use, the nappy body is positioned on a wearer, such as a baby, and the belt is positioned to extend around the entire waist of the nappy body and is firmly secured to itself at either the front or the back depending on the preference of the wearer thereby retaining the nappy body in position on the wearer.

The removable easy-fit belt makes it possible to minimise resources used to manufacture disposable nappies and to provide a better fit than traditional disposable nappies. One belt can be re-used for many nappies and may be made with recyclable materials or (if available) biodegradable materials. The Velcro type fastening system makes it possible to allow a wide range of size adjustments for the one nappy and gives a secure very close fit for the front, back and sides. Not only does it make it possible to replace the traditional side fastening tapes which are integrally connected to nappy bodies, but it also makes it possible to replace the need for elastic in the waist for fitting that is often found in the more expensive disposable nappies.

Belts with no Velcro-type fastener sections at the sides could be used on adult nappies that do not have material that extends right around the waist.

The Velcro type fastener may comprise a plurality of hooks and the outer coverstock of the nappy body has fibres that can retain the hooks.

The applicant is not aware of any nappy systems prior to the subject invention that comprise disposable nappy bodies with separate elastic belts and further comprise "grabbing" the outer "fluffy" coverstock of the nappy bodies with the hooks of Velcro-type type fasteners on the belts.

The belt may comprise a plurality of the Velcro type fasteners at spaced intervals along the length or a part of the length of the belt.

The belt may be made from a soft loop Velcro fastener type material, preferably a stretchy loop material, and comprises small sections of a mini hook Velcro-type fastener secured to an inside surface of the belt at spaced intervals along the length of the belt.

The coverstock may be a soft fluffy biodegradable rayon non-woven material or a similar material to provide a soft comfortable covering while also providing a suitable fiber filament finish which can catch on the Velcro-type fastener or fasteners of the belt.

The nappy body may be a multi-layer laminate construction of the outer coverstock, a waterproof film, and an absorbent fluff paper layer.

The nappy body may comprise elasticised sections on opposite sides of the body.

The elasticised sections may be glued to the nappy body.

The leg guard may be formed by folding and gluing outer sides of the laminate to form narrow elasticised strips of the laminate on opposite sides of the nappy body.

The construction of the nappy body of the nappy of the present invention is such that it can be made from a compostable material or materials, on readily available disposable nappy production lines, minimising costs for set up and production.

According to the present invention there is also provided a pack that comprises a plurality of the disposable nappy body described above and optionally a smaller number, typically one, of the separate belts described above to secure the nappy bodies to a person. Or individual belts may be sold separately.

The disposable nappy body may be made from a compostable material or materials.

According to the present invention there is also provided a compostable disposable nappy body that is shaped to fit around a crotch region of a person wearing the nappy that comprises a multi-layer laminate of:

(a) an outer coverstock made from a soft fluffy biodegradable rayon non-woven material or a similar material to provide a soft comfortable covering while also providing a suitable fiber filament finish which can catch on a Velcro-type fastener or fasteners of a separate belt for retaining the nappy body to the crotch region of a wearer;

(b) a waterproof film for containing solids and liquids, preferably made from a breathable biodegradable starch-based material;

(c) a fluff pulp layer, preferably made from a non-chlorine bleached material, more preferably made from farmed trees or unbleached fluff pulp, that is combined with a super absorbing polymer ("SAP") for absorbency; and (d) an inner lining, preferably made from a hydrophobic compostable hydroentangled or non-woven rayon material or a similar material.

The nappy body may also comprise a stand up leak guard made from a hydrophobic compostable non-woven material, such as rayon and stretched elastic.

According to the present invention there is also provided a disposable nappy body that is shaped to fit around a crotch region of a person wearing the nappy that comprises: (a) a multi-layer laminate of an outer coverstock; a waterproof film for containing solids and liquids; a fluff pulp layer, and an inner lining, and (b) a leg guard on each side of the nappy body that are formed by folding and gluing outer sides of the laminate to form narrow elasticised strips, which can be described as darts, of the laminate on opposite sides of the nappy body, with the strips forming the leg guards.

The laminate may comprise a pair of stretched lengths of elastic glued to each side of the laminate, with the outer one of each pair of Stretched lengths of elastic forming an elasticised leg opening and the inner one of each pair of stretched lengths of elastic forming a leg guard. By forming the leg guards, the area between the legs is reduced and thus forms leg holes without the need to cut the body.

According to the present invention there is also provided a method of manufacturing a disposable nappy that comprises:

(a) forming a multi-layer laminate of an outer coverstock, a waterproof film for containing solids and liquids; an absorbent fluff pulp layer, stretched lengths of elastic, and an inner lining; and (b) forming a leg guard on each side of the nappy body by folding inwardly and then gluing outer sides of the laminate to form narrow elasticised strips, which can be described as darts of the laminate on opposite sides of the nappy body, with the strips forming the leg guards and the darts reducing the area between the legs.

Step (a) may comprise gluing the stretched lengths of elastic between the waterproof film and the inner lining and positioning the fluff paper layer inboard of the stretched elastic.

The method may comprise gluing a pair of stretched lengths of elastic to each side of the laminate, with the outer one of each pair of stretched lengths of elastic forming an elasticised leg hole and the inner one of each pair of stretched lengths of elastic forming a leg guard.

The present invention is described further by way of example with reference to the accompanying drawings, of which.

Figure 1:
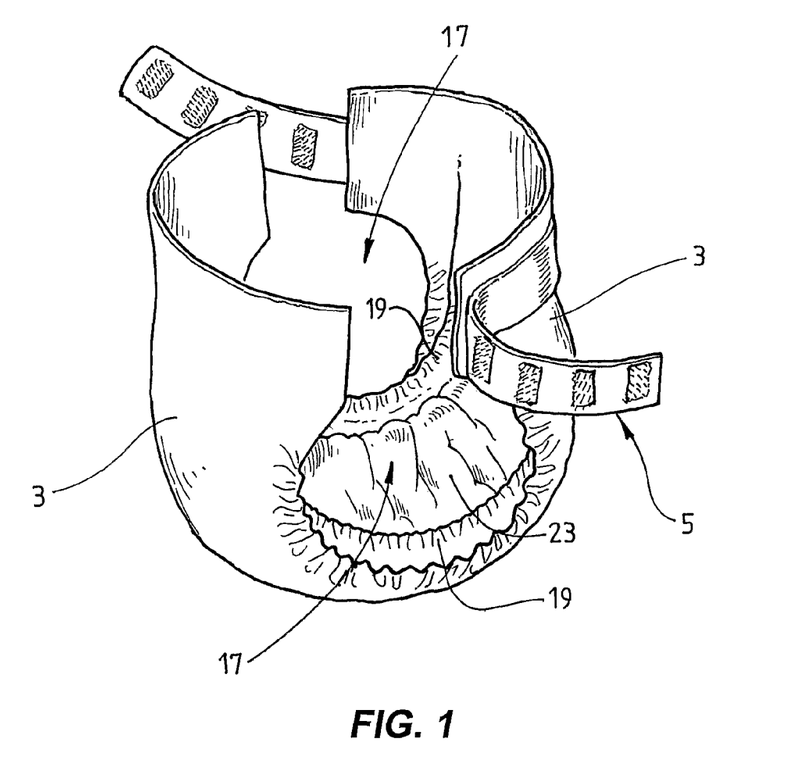
FIG. 1 is a perspective view of one embodiment of a disposable nappy in accordance with the present invention.
Figure 2:
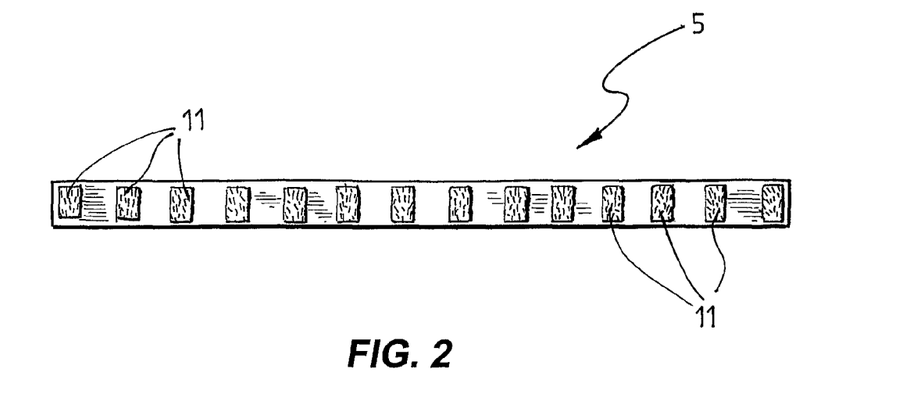
FIG. 2 is a plan view of the belt of the disposable nappy shown in FIG. 1.
Figures 3, 4:
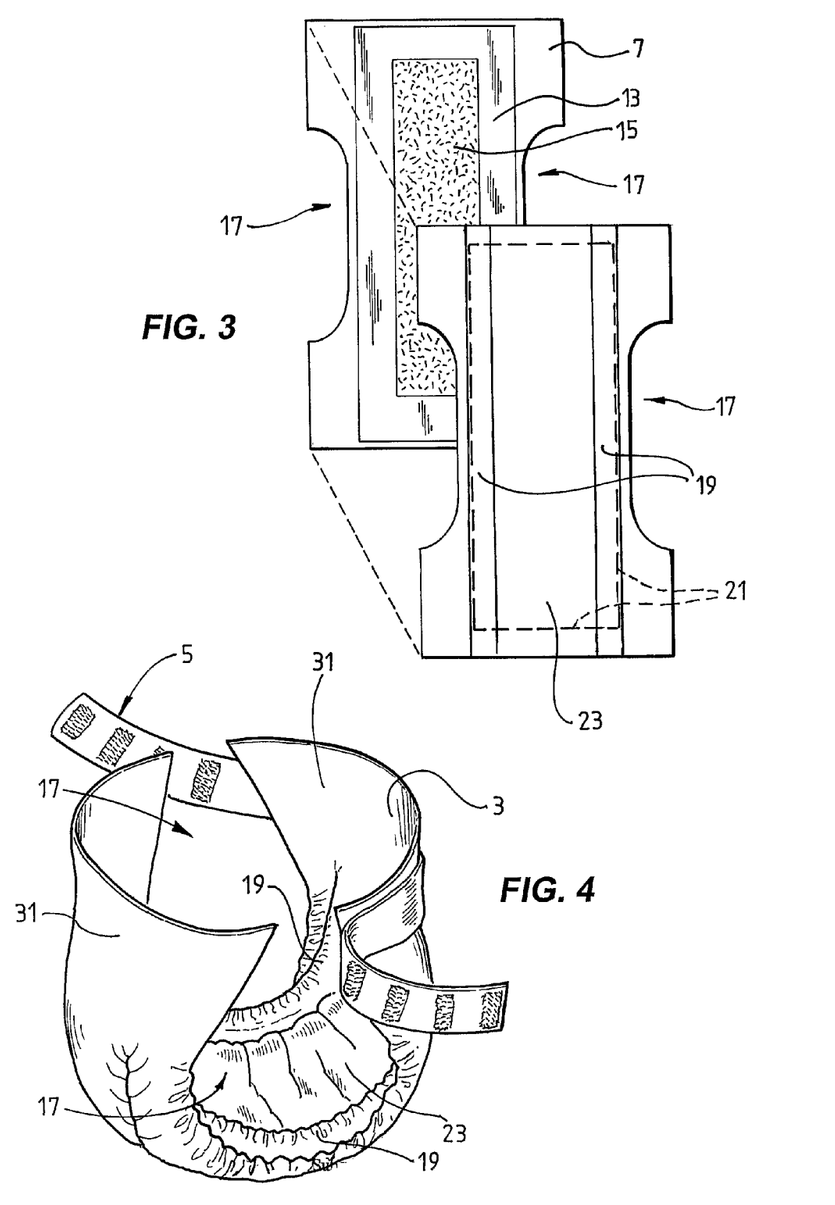
FIG. 3 is an exploded view of the nappy body of the disposable nappy shown in FIG. 1 that illustrates the multi-layer construction of the nappy body.
FIG. 4 is a perspective view of another, although not the only other, embodiment of a disposable nappy in accordance with the present invention.

The disposable nappy shown in FIGS. 1 to 3 comprises:

(a) a nappy body 3 that is shaped to fit around a crotch region of a baby wearing the nappy and, in this regard, is shaped to define elastic leg holes 17; and (b) a separate reusable belt 5 having a plurality of spaced-apart mini hook Velcro-type fasteners 11 along the length of the belt to secure the nappy body 3 to the baby.

The disposable nappy may be sold in packs that comprise a plurality of nappy bodies 3, for example 30 units, and a smaller number, typically one, belt 5.

Alternatively, the disposable nappy may be sold in packs that comprise a plurality of nappy bodies 3 and the belt or a plurality of belts 5 may be sold in separate packs.

With reference to FIG. 3, the nappy body 3 is a multi-layer laminate construction that is formed from rectilinear sheets of material, as described hereinafter, with the leg holes 17 being formed by cutting out sections of the sheets. It is noted here that the nappy body 3 shown in FIG. 4 has leg holes 17 that are not cut-out sections, as described further in relation to the Figure. It is also noted that the nappy bodies 3 shown herein do not require waist elastic or built-in fasteners.

With reference to FIG. 3, the nappy body 3 comprises an outer coverstock 7 made from a soft fluffy biodegradable rayon non-woven (or similar) material to provide a soft comfortable covering while also providing a suitable fiber filament finish which catches on the mini hook Velcro-type fasteners 11 of the belt 5.

The nappy body 3 further comprises a waterproof film 13 for containment of solids and liquids. The film is made from a breathable biodegradable starch-based material.

The nappy body 3 further comprises a non chlorine bleached fluff pulp layer 15 made from farmed trees (or unbleached fluff pulp from farmed trees) that has been combined with a super absorbent polymer "SAP" for absorbency. Regular SAP can be replaced with biodegradable SAP once a suitable product has been developed. To date, starch-based SAP's do not adequately function. Regular SAP can be beneficial to compost where it acts as a "water storing granule".

The nappy body 3 further comprises stand up leak guards 19 along the inside legs of the body 3 and outboard of the fluff paper layer 15. The leak guards 19 are made from a hydrophobic compostable non-woven material (such as rayon and stretched elastic). In the embodiment shown in FIG. 3 the leak guards 19 are formed by separate strips of elasticised material that are glued or otherwise secured to the inner lining 23.

The nappy body 3 further comprises an optional removable flushable liner 21 that can be used to aid in disposing of faecal matter hygienically.

The nappy body 3 further comprises an inner lining 23 which in use contacts the baby wearing the nappy body 3. The inner lining 23 is made from a hydrophobic biodegradable rayon material or similar material, e.g. PLA. (Poly Lactic Acid) in the embodiment shown in FIG. 3. This material replaces the traditional polyethylene coverstocks used in current disposable nappies.

Polyethylene is regularly used for the inner lining of nappy bodies because of its softness and non-absorbing properties, thus providing a stay-dry surface that does not wick liquid from inside the nappy body 3 to the outside. It also is generally non-irritating when in contact with the skin.

The applicant has developed an alternative material for the inner lining 23 which has similar properties but with a significant advantage of being compostable, thus allowing the nappy body 3 to be fully compostable in one compost cycle. The compostable material is preferred by the applicant on environmental grounds, although it is emphasised that the present invention also extends to the use of non-compostable materials for the inner lining 23. The compostable material is a hydroentangled or a regular nonwoven rayon (i.e. a regenerated cellulose, a renewable resource) with minimal binder which has been treated to be hydrophobic. All materials are approved for skin contact and the hydrophobic nature provides a stay dry surface for comfort. It is important to have just enough hydrophobicity but not too much, otherwise leakage will occur due to liquid run-off before it is able to absorb into the absorbent inner core. Rayon is normally hydrophilic but if used like this it would create leakage problems through wicking and would leave a damp surface next to the wearers' skin.

Compostable coverstocks with similar properties could be made using alternative materials.

In use, in order to position the nappy on a baby, the belt 5 is placed on a flat surface with the mini hook Velcro-type fasteners 11 facing up, one end of the nappy body 3 is then placed on the centre of the belt 5, the baby is then placed on the nappy body 3, the front of the nappy body 3 is pulled up between the legs of the baby, one side of the belt 5 is wrapped around the front (or back) where it is held in place as it grips the fibres of the outer coverstock 7, and the other side of the belt 5 is wrapped around to attach firmly to the other end of the belt 5.

The belt 5 (particularly if a stretchy belt) snugs the nappy body 3 close to the body right around the wearer. This eliminates leakage up the front or out the back (a common tendency with regular disposables).

The belt 5 provides a very-comfortable secure fit as it grips the nappy body 3 around the entire waistline (unlike current side tab fasteners). No fiddly threading of belts is required and no slippage of the nappy body 3 around the belt 5 occurs (unlike current nappy belt systems). The nappy body 5 can be opened on one side for inspection as easily as other Velcro-type fastening disposables. When changing the nappy body 3 is required, the belt 5 is simply pulled away for reusing on the next nappy body 3.

The embodiment of the disposable nappy shown in FIG. 4 has the same basic construction as the nappy shown in FIGS. 1 to 3 and the same reference numerals are used to describe the same features.

Figure 5:
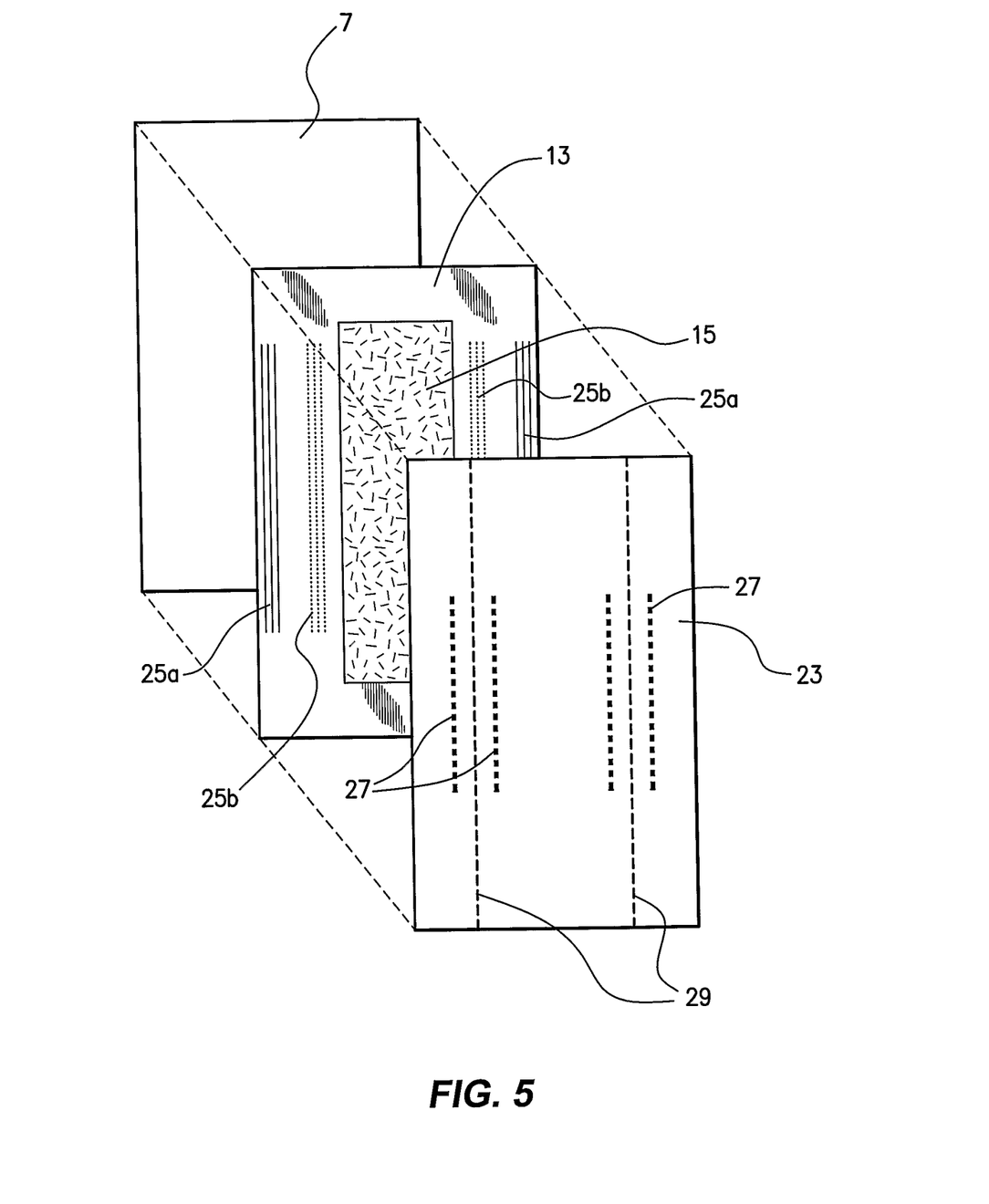
FIG. 5 is an exploded view of the nappy body of disposable nappy shown in FIG. 4 that illustrates the multi-layer laminate construction of the nappy body prior to the final step in one embodiment of a method of manufacturing the nappy body in accordance with the present invention described hereinafter.

FIG. 5 illustrates the construction of the nappy body 3 of the disposable nappy shown in FIG. 4 prior to the final step of a method of manufacturing the nappy body. The as-manufactured form of the nappy body 3 is similar to the nappy body 3 shown in FIGS. 1 to 3. The nappy body 3 in FIG. 4 does not have the cut out leg holes 17 shown in FIGS. 1 to 3 but does have a crease in the outer coverstock 7 where the leg guard 19 is formed.

Figure 6:
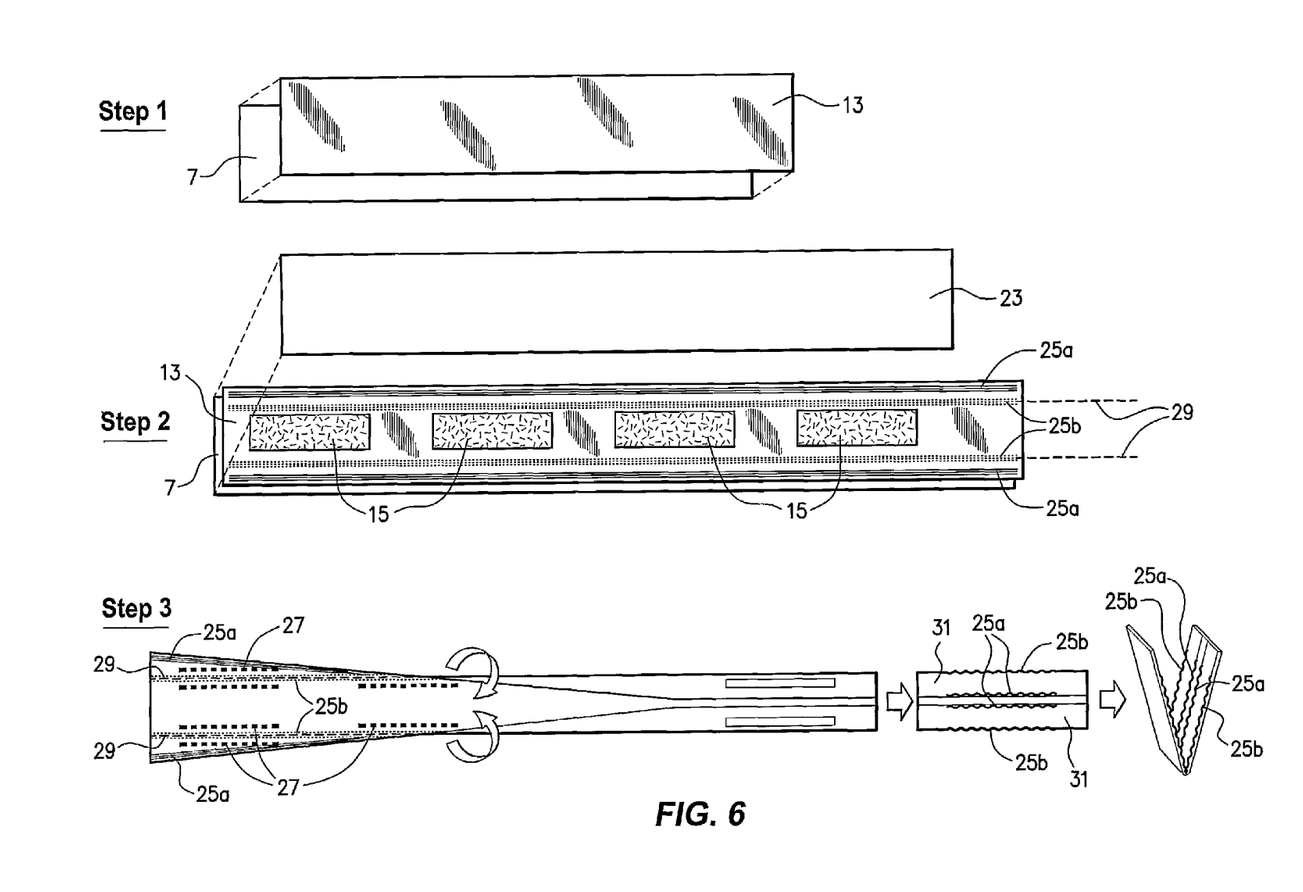
FIG. 6 illustrates diagrammatically the three main steps in the embodiment of the manufacturing method.

As is the case with the FIGS. 1 to 3 embodiment, the FIGS. 4 to 6 embodiment of the nappy body 3 is made from a laminate of rectilinear sheets of material in the form of an outer coverstock 7, a waterproof film 13, an absorbent fluff paper layer 15, and an inner lining 23.

One difference between the embodiments is that the leg holes 17 in the FIGS. 4 to 6 embodiment can be formed from the rectilinear sheets of material shown in FIG. 5 as part of the manufacturing method without requiring cutting of the material.

Another difference between the embodiments is that the leg guards 19 are formed by folding and gluing outer sides of the laminate of the outer coverstock 7, the waterproof film 13 and the inner lining 23 to form narrow elasticised strips of the laminate and are not formed from separate strips of elasticised material that are glued or otherwise secured to the inner lining 23 as is the case with the FIG. 1 to 3 embodiment.

The manufacturing method is carried out advantageously on a standard disposable nappy production line (not shown) and produces a succession of nappy bodies 3. The outer coverstock 7, the waterproof film 13, and the inner lining 23 are unwound from rolls of these materials that are supplied to a series of production stations at which the multi-layer construction of the nappy body 3 is formed successively on the line. The other components of the nappy body 3, namely elastic and the fluff paper 15, and glue which is used in the method, are supplied to the production stations, as described hereinafter.

With reference to FIG. 6, the manufacturing method comprises the following steps.

Step 1

Laminating the outer coverstock 7 and the waterproof film 13 together at a first production station on the line. Note this may be supplied pre laminated rather than be part of the production line.

Step 2

At a series of production stations, carrying out the following stages.

(a) Positioning short lengths of fluff paper 15 and SAP ("fluff paper sections 15") on the waterproof film layer 13 at spaced intervals along the length of the film layer 13 and thereby defining a plurality of nappy body units on the film layer 13.

(b) Gluing a pair of parallel stretched lengths of elastic 25a, 25b along each side of and between the waterproof film 13 and the inner lining 23 outboard of the lengths of fluff paper 15. The glue is only applied in sections that are alongside the fluff paper sections 15. There is no glue in the sections that are between the fluff paper sections 15.

(c) Laminating the inner lining 23 to the above-described assembly, while maintaining the elastic sections in a stretched configuration.

Step 3

Steps 1 and 2 form a multi-layer laminate. Step 3 described below forms this laminate into a plurality of nappy bodies 3 that have the shape shown in FIG. 4.

(a) While continuing to maintain the elastic sections stretched, applying pairs of glue lines 27 on each side of the outer coverstock 7 in sections of the coverstock 7 that are opposite the fluff paper sections 15. The glue lines 27 are on opposite sides of fold lines 29 and only in the area alongside the fluff paper sections 15. The fold lines 29 coincide with the inner stretched elastic sections 25b.

(b) Folding the sides of the laminate inwardly about the fold lines 29 to bring the glue lines 27 on the outer coverstock 7 into contact and thereby forming two glued together narrow folded strips on the sides of each nappy body unit, with each strip including an inner stretched elastic section 25b.

(c) Applying pressure to the narrow folded strips, for example with rollers, to facilitate gluing the folded strips.

(d) Cutting the assembly transversely midway between each nappy body unit, thereby forming successive nappy bodies 3.

It can be appreciated that cutting each nappy body 3 from the production line releases the constraints on the stretched elastic sections 25*a*, 25*b*, with the result that the elastic contracts longitudinally. This release of the constraints facilitates forming the nappy body 3 into the shape shown in FIG. 4.

The right hand end of step 3 of FIG. 6 shows an as-manufactured nappy body 3 an produced at the end of the production line. The contracted elastic sections 25*a*, 25*b* are shown as curved lines to illustrate the contraction of the stretched elastic. It can be appreciated that the outer contracted elastic sections 25*a* effectively pull both sides of this central section of the length of the nappy body 3 inwardly, thereby forming the leg openings 17. The outer sections 31 of the nappy body 3 are not constrained by the elastic and form the wider end sections of the nappy body, as shown in FIG. 4. In addition, the arrangement is such that the inner contracted elastic sections 25*b* and the glued together narrow folded strips of the assembly form the upstanding leg guards 19 shown in FIG. 4.

It can be appreciated from the above that the manufacturing method is a convenient and effective method of manufacturing the nappy body 3 shown in FIG. 4. In particular, the method makes it possible to form leg openings 17 without having to cut material.

In addition, it can be appreciated that the method makes it possible to form the nappy body 3 with the waterproof film 13 being a continuous surface that does not have breaks in the surface.

In particular, the leg guards 19 are formed from the laminate, by selective folding and gluing, and are not separate sections that are glued to a liner material. This construction is an important feature as it minimises resources used by avoiding waste from the leg cut out and the need for extra material to form separate leak guards.

Many modifications may be made to the embodiments of the disposable nappies of the present invention described above with reference to the accompanying drawings without departing from the spirit and scope of the invention.

By way of example, whilst the disposable nappies shown in the Figures are described in the context of being used for babies, the present invention is not so limited and extends to nappies that can be used for children and adults.

Furthermore, whilst the embodiments of the nappy bodies are described in the context of being manufactured from compostable materials, the present invention is not so limited and extends to disposable materials generally.

The invention claimed is:

1. A disposable nappy comprises:
 (a) a disposable nappy body shaped to fit around a crotch region of a person wearing the nappy; and
 (b) a separate reusable belt made of stretchable material that is configured to releasably secure the nappy body to the person,
 wherein the belt includes one or more hook fasteners on an inside surface of the belt and one or more loop fasteners on an outside surface of the belt and the body of the nappy includes an outer coverstock of a material at least in the region that is contacted by the belt that has fibres that are configured to catch onto and retain the one or more hook fasteners on the belt whereby the one or more hook fasteners are located on at least a middle portion of the inside surface and are configured to facilitate locating the nappy body and the belt together by gripping the fibres of the outer coverstock, and wherein the entire belt is configured to wrap completely around the nappy body and be firmly attached to itself to snug the nappy body close to the body of the person.

2. The nappy defined in claim 1 wherein the belt is made with either recyclable materials or biodegradable materials.

3. The nappy defined in claim 1 or claim 2 wherein the outer coverstock fibres engage the hook fasteners of the belt to locate the nappy body in a fixed position against the belt, and one end of the belt is firmly attached to the other end of the belt when wrapped around the nappy body.

4. The nappy defined in claim 1 wherein the belt comprises a plurality of the hook fasteners at spaced intervals along the inside length or a part of the inside length of the belt.

5. The nappy defined in claim 1 wherein the belt comprises small sections of a mini hook fastener secured to an inside surface of the belt at spaced intervals along the length of the belt.

6. The nappy defined in claim 1 wherein the coverstock is one of a biodegradable rayon or PLA non-woven material that provides a soft comfortable covering while also providing a suitable fiber filament finish which can catch on the hook fasteners of the belt.

7. The nappy defined in claim 1 wherein the nappy body is a multi-layer laminate construction of the outer coverstock, a waterproof film, and an absorbent fluff pulp layer.

8. The nappy defined in claim 7 wherein the nappy body comprises elasticised sections on opposite sides of the body.

9. The nappy defined in claim 8 wherein the elasticised sections are glued to the nappy body.

10. The nappy defined in claim 1 wherein the nappy body comprises a multi-layer laminate of:
 (a) an outer coverstock made from a biodegradable rayon non-woven material that provides a covering while also providing a suitable fiber filament finish which is configured to catch on the hook fasteners of the belt for retaining the nappy body to the crotch region of a wearer;
 (b) a waterproof film for containing solids and liquids made from a breathable biodegradable starch-based material;
 (c) an absorbent fluff pulp layer made from farmed trees and/or unbleached fluff pulp and a super absorbing polymer ("SAP") for absorbency; and
 (d) an inner lining, made from a hydrophobic compostable hydroentangled nonwoven rayon material.

11. The nappy defined in claim 1 further comprising a stand up leak guard made from a hydrophobic compostable non-woven material.

12. The nappy defined in claim 1 wherein the nappy body comprises: (a) a multi-layer laminate of an outer coverstock; a waterproof film for containing solids and liquids; an absorbent fluff pulp layer, and an inner lining; and (b) a leg guard on each side of the nappy body that is formed by folding and gluing an outer side of the laminate to form a narrow elasticised strip of the laminate on opposite sides of the nappy body, with the strips forming the leg guards and, in forming the leg guards, narrowing the area between the legs.

13. The nappy defined in claim 12 wherein the laminate comprises a pair of stretched lengths of elastic glued to each side of the laminate, with the outer one of each pair of stretched lengths of elastic forming an elasticised leg opening and the inner one of each pair of stretched lengths of elastic forming a leg guard.

14. The nappy of claim 1 wherein the nappy body comprises a multi-layer laminate of:
 (a) a waterproof film for containing solids and liquids made from a breathable biodegradable starch-based material;

(b) an absorbent fluff pulp layer made from farmed trees and/or unbleached fluff pulp and a super absorbing polymer ("SAP") for absorbency; and (c) an inner lining, made from a hydrophobic compostable hydroentangled nonwoven rayon material.

15. The nappy of claim 1 wherein the coverstock is a biodegradable non-woven material.

16. The nappy of claim 1 wherein the nappy body is compostable.

17. A pack that comprises a plurality of the disposable nappy body defined in claim 1 and at least one separate belt defined in claim 1 to secure the nappy bodies to a person.

\* \* \* \* \*